United States Patent [19]

Abraham-Fuchs et al.

[11] Patent Number: 4,974,602
[45] Date of Patent: Dec. 4, 1990

[54] ARRANGEMENT FOR ANALYZING LOCAL BIOELECTRIC CURRENTS IN BIOLOGICAL TISSUE COMPLEXES

[75] Inventors: Klaus Abraham-Fuchs, Erlangen; Gerhard Roehrlein, Hoechstadt; Siegfried Schneider, Erlangen, all of Fed. Rep. of Germany

[73] Assignee: Siemens Aktiengesellschaft, Berlin and Munich, Fed. Rep. of Germany

[21] Appl. No.: 393,895

[22] Filed: Aug. 15, 1989

[30] Foreign Application Priority Data

Aug. 16, 1988 [DE] Fed. Rep. of Germany ....... 3827799

[51] Int. Cl.$^5$ .............................................. A61N 5/04
[52] U.S. Cl. .................................... 128/731; 128/732
[58] Field of Search ............... 128/731, 732, 734, 696; 364/413.06, 413.03

[56] References Cited

U.S. PATENT DOCUMENTS

| | | | |
|---|---|---|---|
| 4,532,591 | 7/1985 | Osterholm | 364/414 |
| 4,705,049 | 11/1987 | John | 128/731 |
| 4,736,751 | 4/1988 | Gevins et al. | 128/732 |
| 4,753,246 | 6/1988 | Freeman | 128/731 |
| 4,800,895 | 1/1989 | Moberg et al. | 128/731 |
| 4,832,480 | 5/1989 | Kornacker et al. | 128/731 |

OTHER PUBLICATIONS

"Simple Online Detector of Auditory Evoked Cortical Potentials," Mason et al., Med. & Biol. Eng. & Comput., 1977, vol. 15, pp. 641-647.
"New Method for the Study of Spontaneous Brain Activity," Ilmoniemi et al., Biomagnetism 1987, Proceedings of the 6th International Conference on Biomagnetism.

Primary Examiner—Francis Jaworski
Assistant Examiner—George Manuel
Attorney, Agent, or Firm—Hill, Van Santen, Steadman & Simpson

[57] ABSTRACT

In an arrangement for analyzing local bioelectric currents in biological tissue complexes, electrical signals measured by EEG and/or MEG sensors are supplied to a pattern recognition unit in which defined signal patterns are acquired and are provided with time markings to produce "templates." The templates are forwarded to a correlation unit which compares the continuous measured values to the templates, and calculates a correlation coefficient based on the comparison. A threshold definition unit identifies signal patterns from the continuously measured signal which transgress the threshold, and supplies the threshold-transgressing signal patterns to a comparison unit which compares the correlated signal to the threshold-transgressing signal. Signal patterns are selected based on this comparison which are temporally and spatially identical, and are supplied to an averaging unit, which forms temporal averages of the selected signal patterns. A localization unit identifies the geometrical location of any source in the pattern which is pathologically electrically active. These geometrical locations are supplied to a monitor together with a tomographic portrayal of the same region of the subject, and are superimposed on the tomograph display.

14 Claims, 6 Drawing Sheets

ARRANGEMENT FOR ANALYZING LOCAL BIOELECTRIC CURRENTS IN BIOLOGICAL TISSUE COMPLEXES

BACKGROUND OF THE INVENTION

1. Field of the Invention

The present invention is directed to an arrangement for analyzing local bioelectric currents in biological tissue complexes, and in particular to such an arrangement having sensors for measuring electrical or magnetic field quantities generated by the biological electric currents.

2. Description of the Prior Art

An apparatus as described in U.S. Pat. No. 4,736,751 which analyzes brain activities on a statistical basis using a digital computer. Sensors for measuring the electrical and/or magnetic field characteristics of brain currents are distributed in a standard manner over a cranial cap. The measured signals are converted into digital form and stored. The patient being examined is subjected to a set of sensory stimuli which trigger electrical or magnetic fields in localized regions of the brain. The sensors convert these fields into electrical signals which are statistically evaluated and analyzed in order to verify the location of the activity. On the basis of the spatial and temporal-relationships of these spontaneous events, the location of their source and the manner of their propagation can be portrayed on a three-dimensional skull model generated, for example, by computer tomography using nuclear magnetic resonance imaging techniques.

A disadvantage of this known method is that it produces usable results only when the evoked potentials are high enough in magnitude to contrast in a clearly recognizable fashion with the noise level. This generally requires a relatively large number of stimuli to provide a large enough base for the averaging techniques. This renders this known method unsuitable for identifying spontaneous events such as occur, for example, in an epileptic seizure. It is known that the spontaneous events associated with an epileptic seizure can be identified in the electroencephalogram (EEG) as characteristic patterns, referred to as "spike and wave complexes," having a duration of about 200 through 500 ms. These signal patterns are also identifiable between acute seizures, however, with a very different frequency from patient to patient. In extreme cases, such signal patterns can appear every second, or only once a week. As a result of the low signal-to-noise ratio, such interictal signal patterns in the EEG are usually very difficult to recognize, and then only by experienced neurologists. Such signals are virtually unrecognizable with the naked eye in the magnetoencephalogram (MEG). The point of origin of such spontaneously appearing single patterns is interpreted as an epileptogenous seat. The goal of the interpretation of an EEG or MEG in epilepsy diagnostics is to localize the location of this seat as exactly as possible. It is also of significance for the neurologist to obtain information regarding the spatial propagation of signal-forming, electrical excitations, both within a signal pattern and in successive, different signal patterns. Such information has heretofore only been able to be obtained using invasive techniques, such as EEG depth electrodes. Even these invasive techniques yield only a limited amount of information. Moreover, a time-resolving localization is difficult or impossible to achieve because, due to the low signal-to-noise ratio, a localization having the required precision cannot be obtained based on a single signal event, and usually a sufficient number of such events is not available for a reliable averaging.

In the article "New Method for the Study of Spontaneous Brain Activity," Ilmoniemi et al., Biomagnetism 1987, Proceedings of the 6th International Conference on Biomagnetism, correlation of the local patterns of brain signals is disclosed for the purpose of recognizing spike-wave complexes. Such correlation is undertaken, however, only in an EEG channel for the detection of epileptic and alpha activities. This method is adequate only when a significant event is unambiguously recognized in a channel. It is known, however, that significant correlations of spike-wave complexes, in the context of the signal-to-noise ratio which occurs in practice, cannot be observed at all using the simple correlation function, and can only be poorly observed in the spatially and chronologically averaged correlation functions of an MEG.

SUMMARY OF THE INVENTION

It is an object of the present invention to provide an arrangement for processing electrical signals corresponding to electrical or magnetic field strengths obtained from sensors arranged spatially distributed with respect to a biological tissue complex to be examined, such that defined signal patterns appearing within a time interval can be used as basis for searching for and identifying similar patterns in the continuous signal.

It is a further object of the present invention to process the electrical signals so that the chronological appearance and spatial allocation of the similar patterns can also be identified.

The above objects are achieved in an arrangement having means for recognition of individual signal patterns derived from the electrical signals corresponding to the measured values, the signal patterns being temporally limited (i.e., subjected to a "time window") to form "templates", and the templates are stored. Another unit undertakes a spatial and chronological correlation of the continuously measured values with the stored signal pattern templates, and forms a space-time function and a correlation signal. A threshold definition unit identifies signal patterns from the continuously measured values which transgress the threshold, and the threshold-transgressing signals are compared in a comparison unit with the correlation signal. This results in a set of temporally and spatially identical signal patterns, which have been selected according to the aforementioned predetermined similarity and threshold criteria. These selection signal patterns are supplied to a further unit which undertakes a temporal averaging of the patterns. The output of the averaging unit is supplied to a localization unit, which spatially allocates the average signal patterns to signal-triggering current sources. Information, such as coordinates, of the current sources is supplied to a display to which a computed tomography image is also supplied, so that the current source can be superimposed on the tomography image.

The spatial and temporal correlation of the averaged signal patterns obtained in accordance with the principles of the present invention provides useable signal values which adequately contrast with noise, and thus permits reliable evaluation of those signals.

In a further embodiment of the invention, a filter stage can be provided for removing known noise frequencies such as, for example, the line frequency or certain periodically appearing, spontaneous biosignals, from the signals in the channels of the sensors.

In another embodiment of the invention, the spatial correlation is undertaken by averaging over the correlation function over the allocated time interval of the signal pattern, and the temporal correlation function, with subsequent averaging, is formed over the allocated space according to defined mathematical relationships. These two correlation signals can then be multiplied, so that peak signals are obtained having a particularly clear contrast with the noise.

In a further embodiment of the invention, the correlated signal is intermediately stored in a memory, and is then supplied to a calculating unit which calculates the frequency distribution, in the form of a histogram, of the stored correlated signal, and the histogram is supplied to a threshold acquisition unit which, on the basis of a defined deviation of the frequency distribution from a normal Gaussian distribution curve, identifies a similarity threshold which is characteristic for the signal section being analyzed. This similarity threshold is supplied to the aforementioned comparison unit, and is used to set the threshold against which the intermediately stored correlation signal is compared. Those signal sections which transgress the threshold are supplied from the memory to the aforementioned averaging unit, for further processing as described above.

When undertaken by standard digital computers, the required arithmetic operations undertaken by the arrangement disclosed herein require considerable calculating time. In a further embodiment of the invention, therefore, an array processor computer is provided in combination with an algorithm for a so-called fast convolution. This achieves a significant shortening of the calculating time, and allows results to be obtained shortly after execution of the examination, so that the patient can remain connected to the measuring arrangement for a possible repetition or follow-up acquisition of data.

DESCRIPTION OF THE PREFERRED EMBODIMENTS

Figure 1:
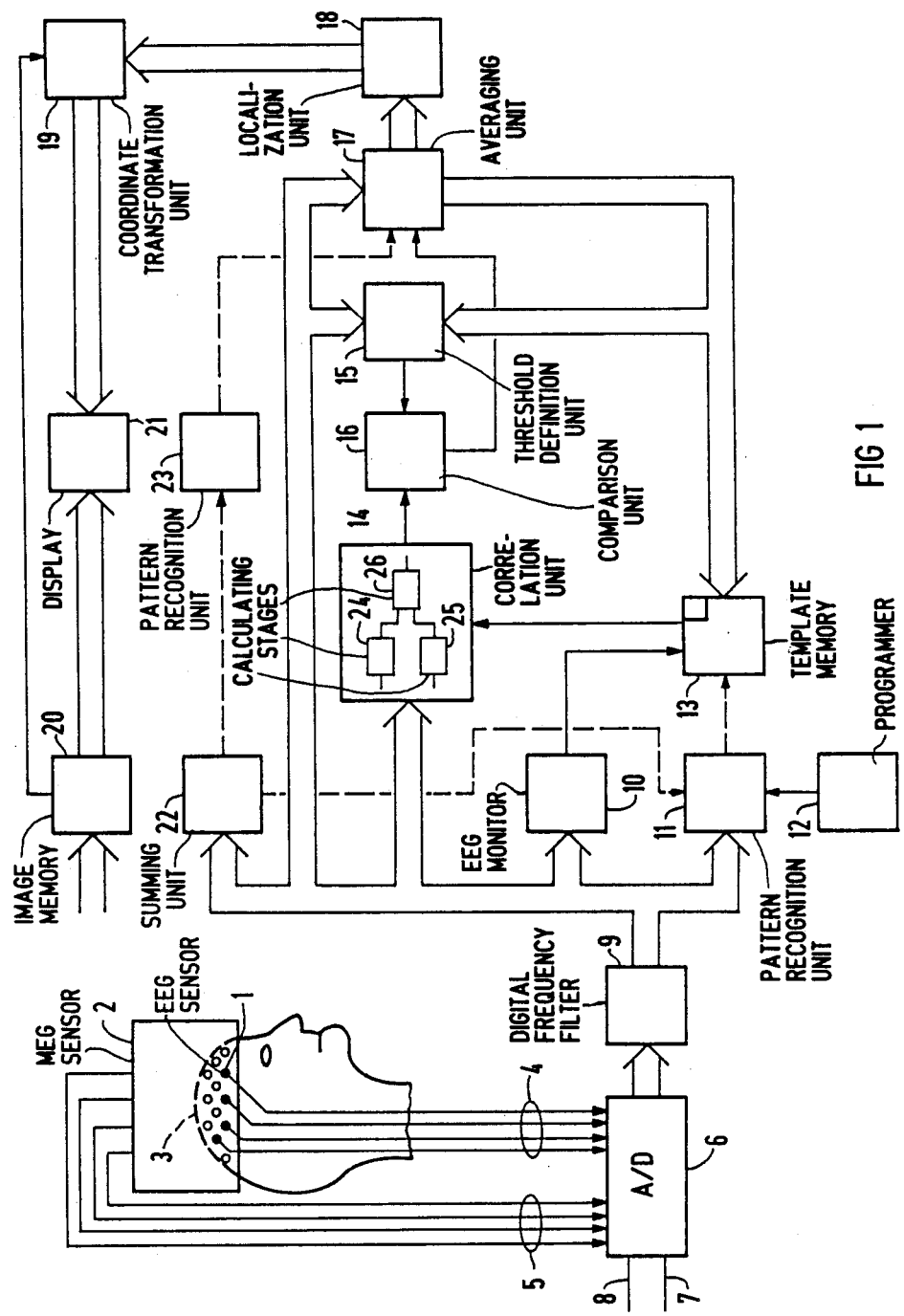
FIGS. 1 is a schematic block diagram for an arrangement for measuring local bioelectric currents in biological tissue complexes constructed in accordance with the principles of the present invention.

In the arrangement shown in FIG. 1, the sensor electrodes of an electroencephalograph (EEG) and a SQUID sensor 2 of a multi-channel magnetoencephalograph (MEG) are arranged spatially distributed over the cranial cap 3 of a patient. The sensors generate electrical signals in a known manner corresponding to the measured electrical or magnetic fields. These electrically signals are supplied via lines 4 and 5 to an N-channel analog-to-digital converter 6. The analog-to-digital converter 6 can also be supplied with trigger signals from an EKG apparatus (not shown) via a lead 7, and with trigger signals controlled by respiration via a lead 8. These trigger signals serve in a known manner to trigger the acquisition of measured values within defined limits which are temporally determined by the respiratory frequency and/or heart activity. The digital signals of the EEG and MEG channels are conducted to an N-channel digital frequency filter 9, which filters known periodically appearing noise frequencies out of the incoming signal. These periodically appearing noise frequencies may be, for example, the line frequency or excitation centers of the alpha waves emanating from the brain. The output of the filter 9 is supplied to an EEG monitor 10, which displays the output signals in an interpretable form (digital or analog) making them accessible to analysis by the physician.

The output of the filter 9 may be alternatively or simultaneously supplied to a programmable pattern recognition stage 11, instead of or in addition to the EEG monitor 10. The pattern recognition stage 11 is programmable by a programmer 12 to recognize specific signal patterns. Thus either signals patterns which have been recognized based on the criteria entered via the programmer 12, or signal patterns which have been recognized by a physician on the EEG monitor by a physician and have been permitted to pass therethrough, are supplied to a template memory 13. The recognized signal pattern, after recognition, must be temporally defined, i.e., a starting time and an ending time must be defined. Such a temporally defined signal pattern is referred as a template. The starting and ending times of a recognized pattern can be set in the EEG monitor 10 or the pattern recognition unit 11 in a known manner. The template recognized and defined in this manner is stored in the template memory unit 13.

The continuously measured signal at the output of the filter 9 is also supplied to a correlation unit 14 which can call the template stored in the template memory 13 to compare the template to the continuously entering signal. For that purpose, a time interval, defined by the template, is superimposed on the entering data as a "time window." In each time window, the correlation coefficient of each temporal signal pattern is calculated according to the following mathematical relationship in a first calculating stage 24, and is averaged over all measuring locations:

$$K_R(t_i) = \frac{1}{N} \sum_{C_i=C}^{C_N} \frac{\sum_{\tau_i=\tau_o}^{\tau_M} S_{ci}(t_i + \tau_i) S_{ci}(\tau_i)}{\left(\sum_{\tau_i=\tau_o}^{\tau_M} S_{ci}^2(t_i + \tau_i)\right)^{\frac{1}{2}} \left(\sum_{\tau_i=\tau_o}^{\tau_M} S_{ci}^2(\tau)\right)^{\frac{1}{2}}}$$

The correlation coefficient of the signal curves in the same time window is likewise calculated at each measuring location in a second calculating stage 25 in the correlation unit 14 according to the following formula:

$$K_T(ti) = \frac{1}{M} \sum_{\tau_i=\tau_o}^{\tau_M} \frac{\sum_{C_i=C_1}^{C_N} S_{ci}(ti+\tau_i) S_{ci}(\tau_i)}{\left(\sum_{C_i=C_1}^{C_N} S_{ci}^2(ti+\tau_i)\right)^{\frac{1}{2}} \left(\sum_{C_i=C_1}^{C_N} S_{ci}^2(\tau_i)\right)^{\frac{1}{2}}}$$

and is averaged over all points in time within the time window. The functions for the temporal and spatial correlation calculated as above are multiplied to obtain $K_{RT}(ti) = K_R(ti) \cdot K_T(ti)$. In the above formulae, $C_1 \ldots C_N$ are the N magnetic measuring channels in an arbitrary topical distribution, $S_{Ci}(ti)$ is the magnetic signal in a channel $C_i$ at a point in time ti, $\tau_o \ldots \tau_i \ldots \tau_M$ denote the time interval of the template, beginning at $\tau_o$ and ending at $\tau_M$, with $\tau_i$ indicating a point in time of the time interval with $\tau_o \leq \tau_i \leq \tau_M$, $K_T(ti)$ is the temporal correlation factor (correlation coefficient of the template and the measured signal at a point in time ti), $K_R(ti)$ is the spatial correlation factor (correlation coefficient of the template and the measured signal at a point in time ti), and $K_{RT}(ti)$ is the space-time correlation factor.

It is also possible to provide a single calculating stage within the correlation unit 14 which undertakes the correlation according to the formula:

$$K_{RT}(ti) = \frac{\sum_{C_i=C_1}^{C_N} \sum_{\tau_i=\tau_o}^{\tau_M} S_{ci}(ti+\tau_i) S_{ci}(\tau_i)}{\left(\sum_{C_i=C_1}^{C_N} \sum_{\tau_M=\tau_o}^{\tau_M} S_{ci}^2(ti+\tau_i)\right)^{\frac{1}{2}} \left(\sum_{C_i=C_1}^{C_N} \sum_{\tau_i=\tau_o}^{\tau_M} S_{ci}(\tau_i)\right)^{\frac{1}{2}}}$$

wherein the symbols and functions are as identified above.

The space-time correlation factor $K_{RT}(ti)$ formed as described above is supplied to a comparison unit 16 which compares this correlation factor to a threshold, the threshold being supplied from a threshold definition unit 15, which is supplied with the output of the filter 9. If the threshold is exceeded, entry of the signal pattern from the output of the filter 9 is enabled into the averaging unit 17. The averaging unit 17 forms an average signal of all of the signal patterns recognized based on the aforemention criteria over time at all measuring locations. This average signal is supplied to the template memory 13 and to the threshold definition unit 15 for ongoing correction of the template. The average signal is also supplied from the averaging unit 17 to a localization unit 18. The localization unit 18 calculates the geometrical location of any pathologically electrically active source which has appeared in the patterns, and supplies this data to a coordinate transformation unit 19. The coordinate transformation unit 19 has another input from which coordinate information is supplied from an image memory 20, in which a tomographic image from any suitable type of tomographic imaging system, is stored. The coordinate transformation unit 19 transforms the coordinate system of the EEG or MEG measurement into the coordinate system of the image in the memory 20. This permits the image from the memory 20 to be represented on a display 21 as a three-dimensional image with the location of the pathologically electrically active source superimposed thereon.

An alternative method for locating very weak signal patterns, which can achieve better results in some cases, includes the step of summing the signals of all channels in a summing unit 22. The output of the summing unit 22 is then supplied to a pattern recognition unit 23, which corresponds to the pattern recognition unit 11, and may also be programmable, however a separate programmer is not shown in FIG. 1. The recognized patterns from the pattern recognition unit 23 are supplied to the averaging unit 17, instead of the signal coming from the comparison unit 16, and processing is done in the same way as described above. Another alternative is to supply the output of the summing unit 22 to the pattern recognition unit 11, for use in template definition. This type of signal processing is particularly suited if only MEG signals are acquired.

Figure 2:
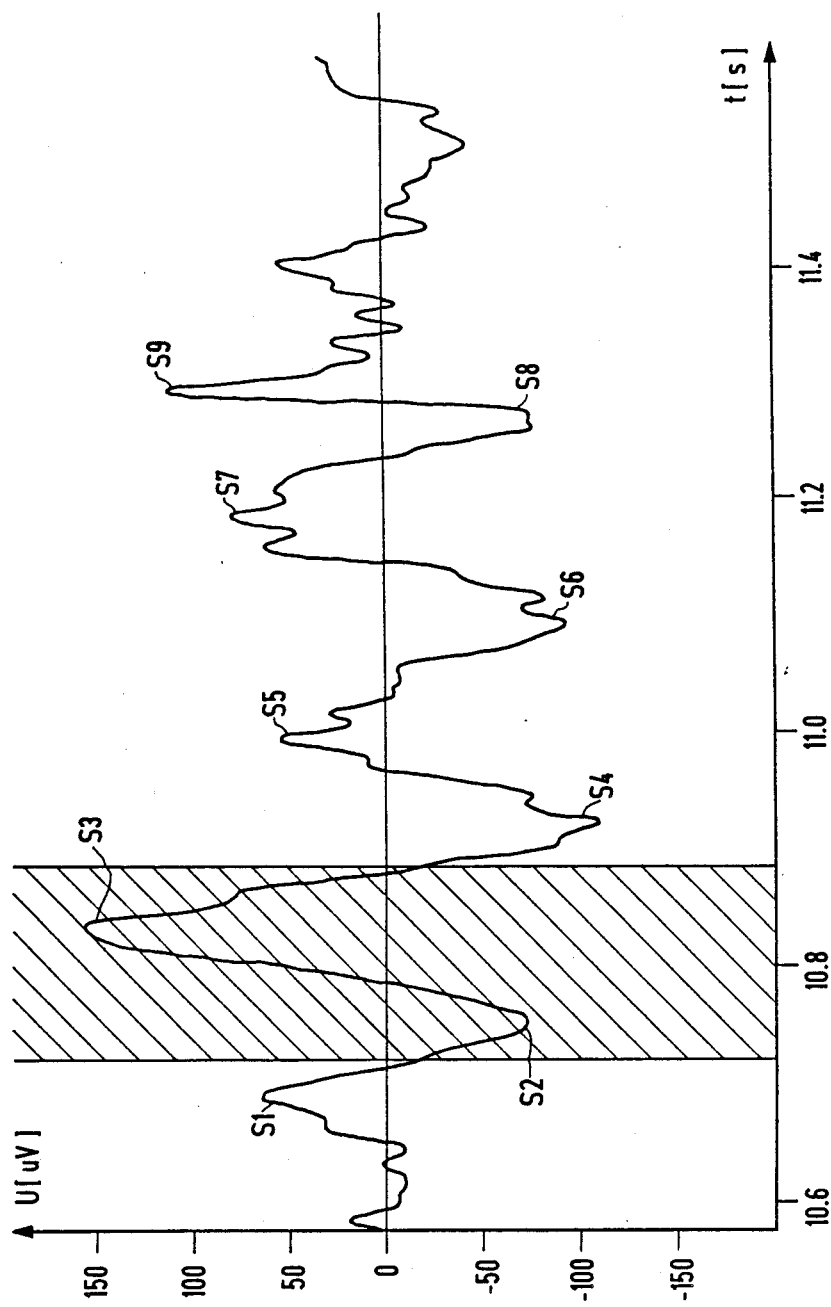
FIG. 2 is a graph showing a typical signal pattern of a spontaneous event in the brain of a patient.

An electrocephalogram from a representative EEG sensor 1 is shown in FIG. 2. The approximately triangular portions S1 through S9 of the signal can be noticed with the naked eye, and are referred as "sharp waves" by neurologists. The pathological significance of these signal portions is, however, not clear. It is apparent that the signal portions S2 and S3 differ rather markedly from the other signal portions, and therefore the S2–S3 complex is selected as a template, with the time window for the template being shown shaded. As described above, this can be done either automatically in the pattern recognition unit, based on criteria entered via the programmer 12, or can be done by the neurologist based on his or her viewing of the EEG monitor.

Figure 3:
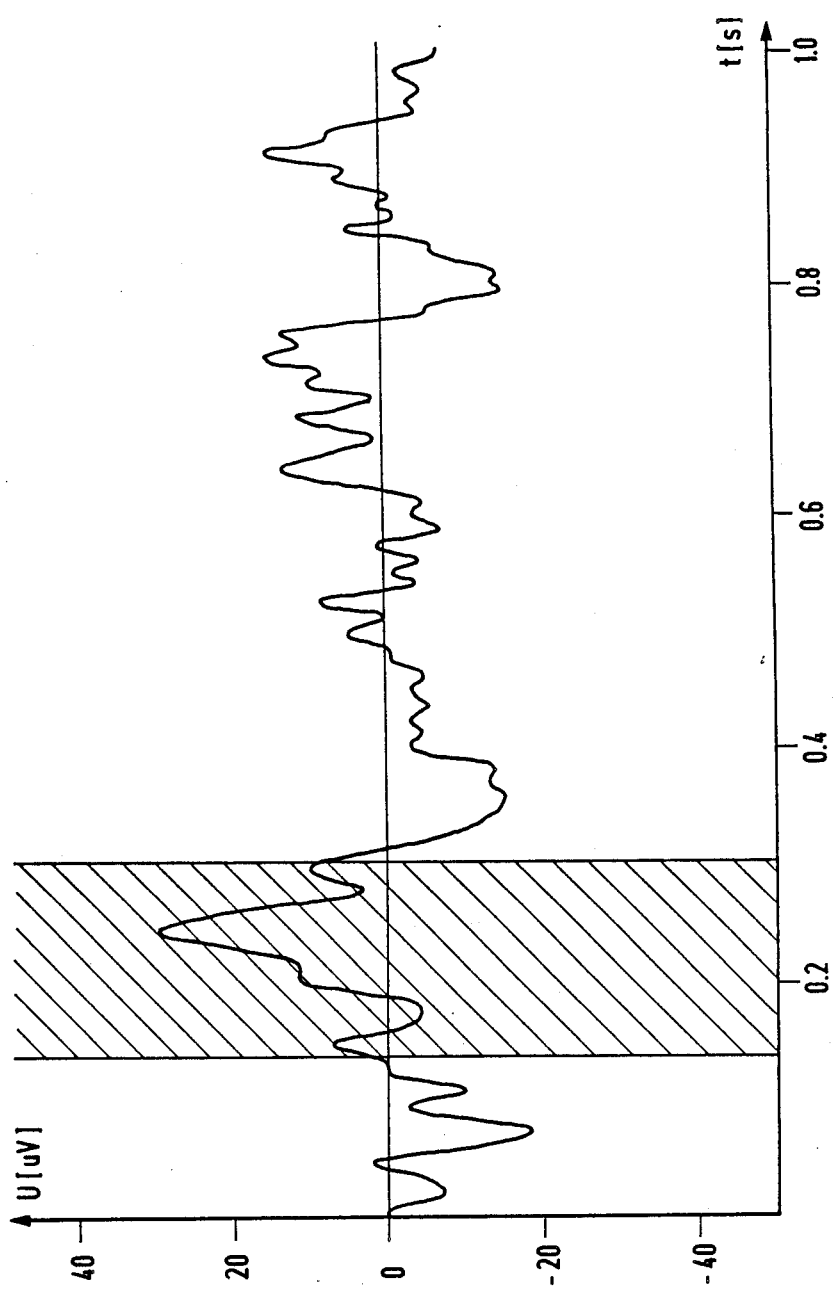
FIG. 3 is an averaged signal generated by the arrangement of FIG. 1 after a space-time correlation.

The averaged signal obtained after space-time correlation, as described above, is shown shaded for the same EEG channel in FIG. 3. The signal pattern averaged in this manner meets the criteria of a pathological "spike-wave complex" considerably more clearly than the complex before processing shown in FIG. 2. The spike-wave complex shown in FIG. 3, however, has a more complicated structure than could be observed in known EEG systems.

The arrangement described above permits the recognition of specific events within a continuous recording of bioelectric or biomagnetic signals with a digital, space-time correlation analysis on the basis of the comparison of the continuously incoming signal with a stored, defined signal pattern (template).

As a result of this comparison, a variable between $-1$ and $+1$ is obtained at each comparison time in the data set for the correlation coefficient. This variable constitutes a measure of the similarity of the signal recorded within the time window defined by the signal pattern for each comparison time. If the correlation coefficient is $+1$, the coincidence is maximum with the same operational sign. The poorest coincidence results in a correlation coefficient of zero. When the correlation efficient is $-1$, the coincidence is maximum with a reversed operational sign of the signals. In a further embodiment of the invention, described in detail below, the goal is not only to identify those signal regions or complexes within the signal sequence which are identical to the template, but also to document a characteristic degree of similarity. Those signal regions which exceed a similarity threshold characteristic for the particular data set are then identified.

Figure 4:
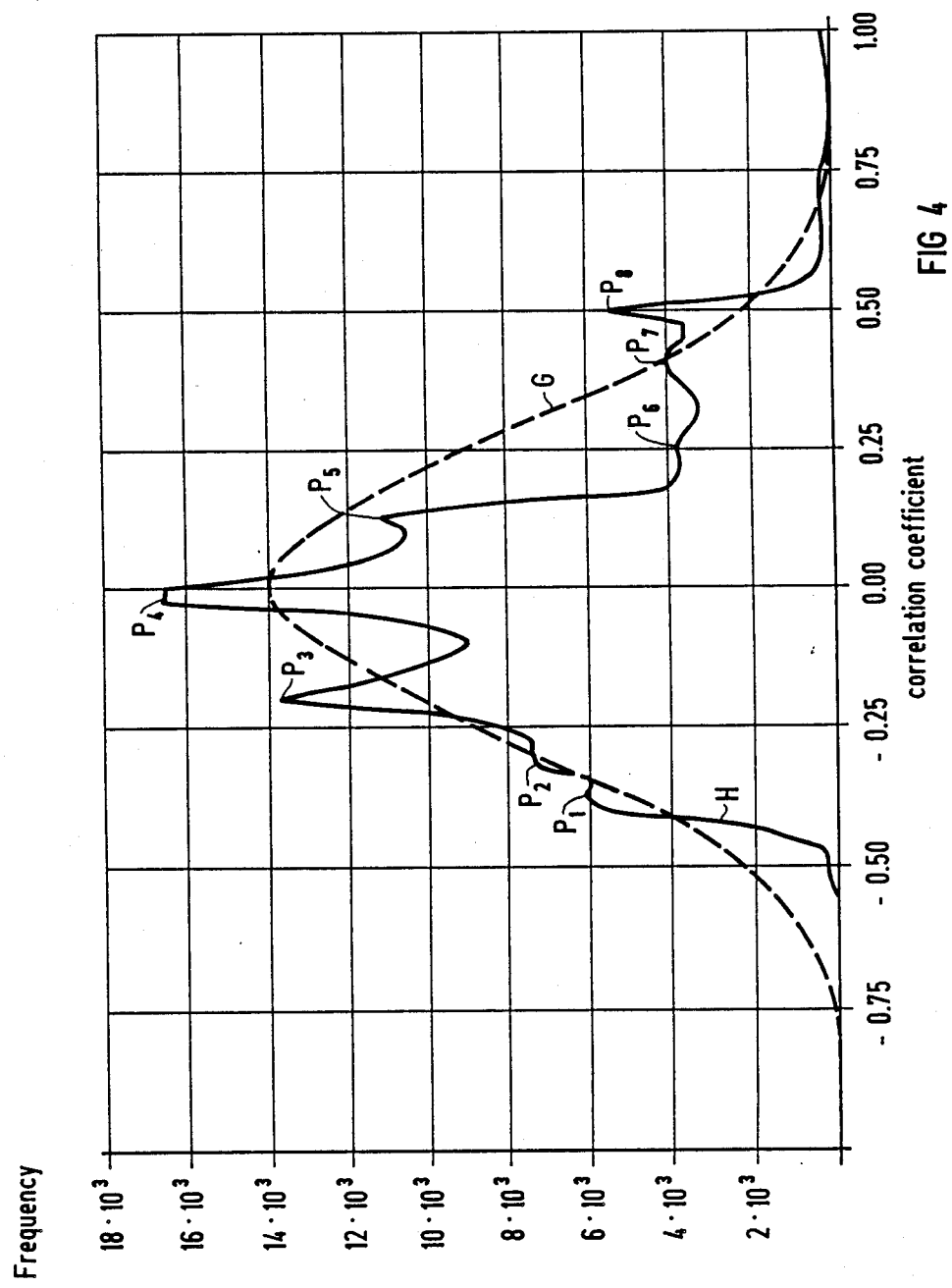
FIG. 4 is a graph showing a typical distribution curve of the frequency of appearance of a defined similarity (correlation coefficient) between the continuing measured signal and a comparison signal.

A graph showing the frequency of the appearance of all possible similarity degrees between the measured signal and the comparison signal is shown in FIG. 4, with reference to a typical distribution curve. If the signal region under investigation consists only of white noise, the frequency distribution of all correlation coefficients represents a Gaussian normal distribution, as shown by the dashed line curve G in FIG. 4. The solid line curve H represents a histogram of the normal frequency distribution based on a history of measurements. Each deviation from the histogram curve H is a clear indication that signal complexes are present which, dependent on the size of their respective correlation coefficient, have a more or less pronounced similarity to the prescribed curve path of the template. Such deviations are identified by peaks $P_1$ through $P_8$ which are superimposed on the Gaussian distribution curve G. The degree of similarity increases the closer such a peak lies to the value $+1$. The base point lying at the left (i.e., in the direction of lower correlation coefficience) in a particular peak which is closest to the correlation coefficient $+1$ defines the sought characteristic similarity threshold. In the example shown in FIG. 4, the peak $P_8$ lies closest to the correlation coefficient $+1$, and the relevant base point for that peak is at approximately 0.48. Each transgression of this threshold defines a point in time in the signal under investigation which has adequate similarity to the template.

Figure 5:
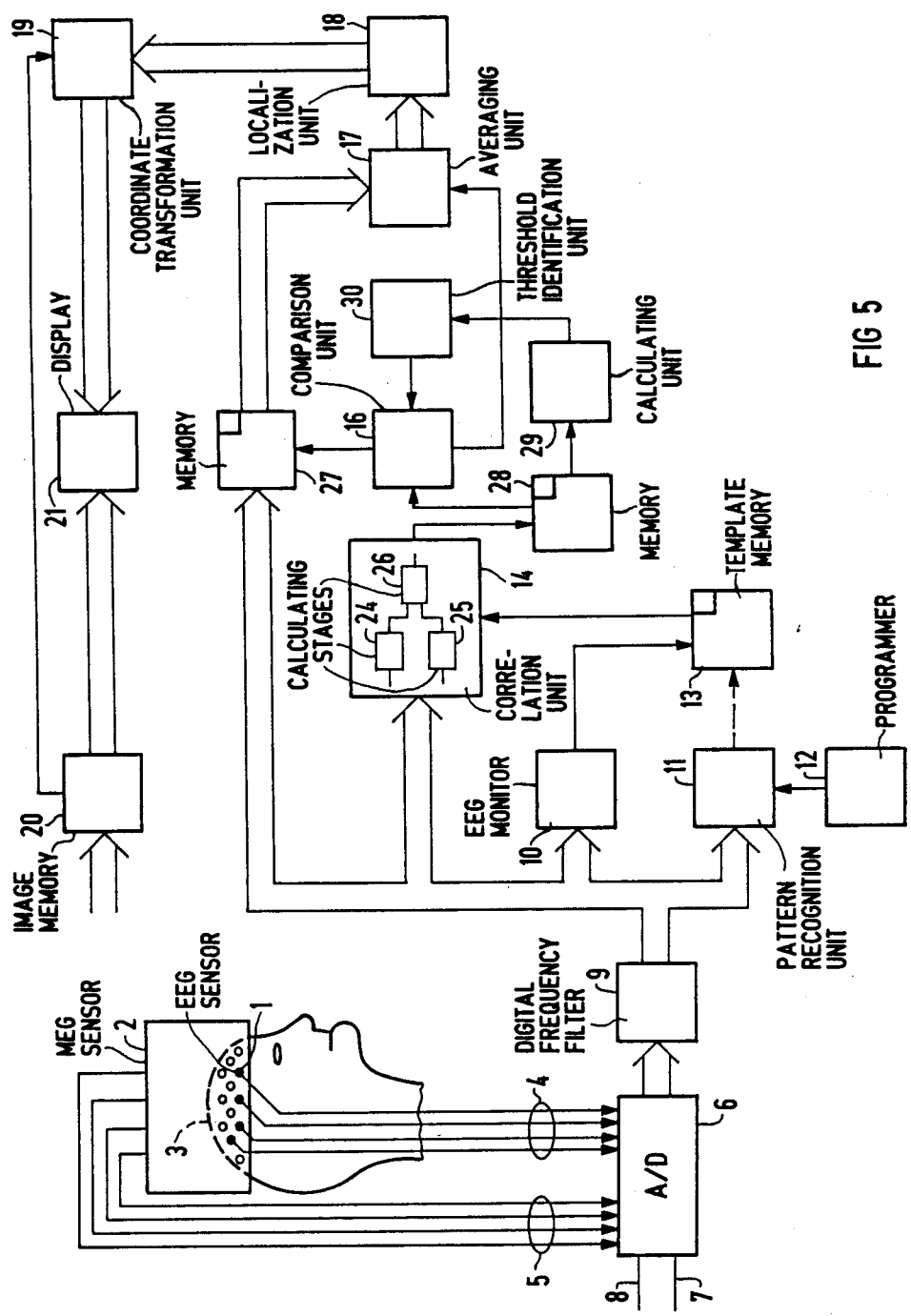
FIG. 5 is a schematic block diagram of a further embodiment of an arrangement for measuring local bioelectric currents in biological tissue complexes constructed in accordance with the principles of the present invention.

A circuit for identifying the similarity threshold is shown in FIG. 5. Those components having the same function as described in connection with FIG. 1 are provided with the same reference symbols, and need not be described again.

In the circuit of FIG. 5, the measured signal, at the output of the filter 9, is stored in a memory 27, and the correlation signal, formed in the correlation unit 14 by the calculating stages 24, 25 and 26, is stored in a memory 28. The signal from the memory 28 is supplied to a calculating unit 29 for calculating the histogram, as shown in FIG. 4, and is simultaneously supplied to the comparison unit 16. The histogram signal at the output of the calculating unit 29 is supplied to a threshold identification unit 30 which determines the characteristic threshold from the distribution curve, and supplies this characteristic threshold to the comparison unit 16. In the comparison unit 16, the stored correlation signal from the memory 28 is compared to the characteristic threshold from the threshold identification unit 30. If the threshold is transgressed, the comparison unit 16 supplies an enabling signal to the memory 27 to permit the signal portion, corresponding to the point in time identified by the transgression, to be supplied to the averaging unit 17. This signal portion is then evaluated by the localization unit 18 in the manner described above in connection with FIG. 1. Those signals which exceed a characteristic similarity threshold, related to the template signal, are thus acquired for evaluation in this manner, so that a recognition of the sought signal complexes, with subsequent averaging, is possible, even given a unknown noise amplitude or given a combination of the overall signal consisting of the input signal plus noise and other characteristic signal complexes.

Figure 6:
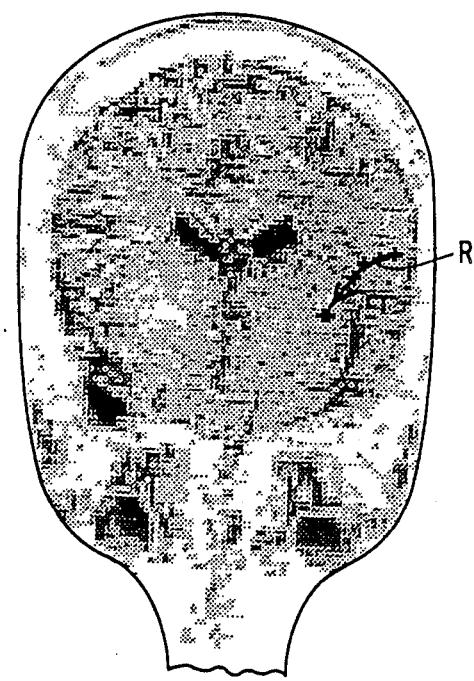
FIG. 6 shows a tomogram of the brain superimposed with a typical excitation path of a spontaneous event obtained in accordance with the principles of the present invention.

A representation of the image which can be seen on the display 21 of the arrangement disclosed herein is shown in FIG. 6. The localization image with its coordinates transformed to those of the tomography system, is brought into congruence with the image from the image memory 20, and the region R of the pathological electrical activity is clearly recognizable, such as by the points identified with crosses forming a line characterizing the chronological activity path.

Although modifications and changes may be suggested by those skilled in the art, it is the intention of the inventors to embodiment within the patent warranted hereon all changes and modifications as reasonable and properly come within the scope of their contribution to the art.

We claim as our invention:

1. An arrangement for analyzing local bioelectric currents in biological tissue complexes in a patient comprising:
   a plurality of sensors adapted to be spatially distributed over a region of a patient in which a biological tissue complex to be analyzed is disposed, said sensors generating electrical signals based on measured filed quantities generated by local bioelectrical currents;
   means for recognizing individual signal patterns within said electrical signals and for temporally limiting said signal patterns to form a template for each signal pattern;
   means for storing said templates;
   means for spatially and chronologically correlating said electrical signals, after formation of said templates, with said stored templates to form a space-time function and a correlation signal derived from said space-time function;
   means for deriving a significant threshold for said correlation signal from said electrical signals;
   means for comparing said correlation signal to said threshold and for enabling entry, on the basis of the comparison, of selected ones of the identified signal patterns into a means for chronologically averaging said identified signal patterns;
   means for identifying a localized spatial source within said biological tissue complex from the averaged identified signal patterns; and
   means for superimposing an image identifying the location of said source on a separately generated tomogram of said biological tissue complex.

2. An arrangement as claimed in claim 1, wherein said sensors are sensor which generate said electrical signals corresponding to measured electrical field quantities generated by said biological electrical currents.

3. An arrangement as claimed in claim 2, wherein said sensors are sensors which generate said electrical signals corresponding to measured magnetic field quantities generated by said biological electrical currents.

4. An arrangement as claimed in claim 1, wherein said electrical signals are analog electrical signals, and further comprising:
   means for converting said analog electrical signals into corresponding digital electrical signals; and
   means for digitally filtering selected noise frequencies out of said digital electrical signals.

5. An arrangement as claimed in claim 1, wherein said means for recognizing individual signal patterns is a means for automatically recognizing individual signal patterns.

6. An arrangement as claimed in claim 1, wherein said means for automatic recognition of individual signal patterns is programmable, and further comprising means for entering selected programmable criteria for recognition of individual signal patterns into said means for automatic recognition of individual signal patterns.

7. An arrangement as claimed in claim 1, wherein said means for recognition of individual signal patterns is a means for visual manual recognition of individual signal patterns.

8. An arrangement as claimed in claim 1, wherein said means for spatially and temporally correlating comprises:

a first calculating means for forming a spatial correlation function $K_R(t_i)$ and for averaging said spatial correlation function over a time interval defined by the length of said templates according to the formula $$K_R(t_i) = \frac{1}{N} \sum_{C_i=C_1}^{C_N} \frac{\sum_{\tau_i=\tau_o}^{\tau_M} S_{C_i}(t_i + \tau_i) S_{C_i}(\tau_i)}{\left(\sum_{\tau_i=\tau_o}^{\tau_M} S^2_{C_i}(t_i + \tau_i)\right)^{\frac{1}{2}} \cdot \left(\sum_{\tau_i=\tau_o}^{\tau_M} S^2_{C_i}(\tau_i)\right)^{\frac{1}{2}}}$$

second calculating means for forming a temporal correlation function averaged over a space defined by the spatial distribution of said signal sensors constituting said templates according to the formula $$K_T(t_i) = \frac{1}{M} \sum_{\tau_i=\tau_o}^{\tau_M} \frac{\sum_{C_i=C_1}^{C_N} S_{C_i}(t_i + \tau_i) \cdot S_{C_i}(\tau_i)}{\left(\sum_{C_i=C_1}^{C_N} S^2_{C_i}(t_i + \tau_i)\right)^{\frac{1}{2}} \cdot \left(\sum_{C_i=C_1}^{C_N} S^2_{C_i}(\tau_i)\right)^{\frac{1}{2}}}$$

and third calculating means for multiplying $K_R(t_i)$ and $K_T(t_i)$, wherein $C_1 \ldots C_N$ denote N sensor measuring channels in an arbitrary topical distribution relative to said biological tissue complex, $S_{C_i}(t_i)$ denotes a signal in the channel $C_i$ at a point in time $t_i$ and $\tau_o \ldots \tau_i \ldots \tau_M$ denote said time interval of a template, beginning at $\tau_o$ and ending at $\tau_M$ with samples at a time $\tau_i$ in said time interval, with $\tau_o < \tau_i < \tau_M$.

9. An arrangement as claimed in claim 1, wherein said means for spatially and temporally correlating comprises means for spatially and temporally correlating said electrical signals with said templates to form said spacetime correlation function $K_{RT}(t_i)$ according to the formula $$K_{RT}(t_i) =$$

$$\frac{\sum_{C_i=C_1}^{C_N} \sum_{\tau_i=\tau_o}^{\tau_M} S_{C_i}(t_i + \tau_i) \cdot S_{C_i}(\tau_i)}{\left(\sum_{C_i=C_1}^{C_N} \sum_{\tau_i=\tau_o}^{\tau_M} S^2_{C_i}(t_i + \tau_i)\right)^{\frac{1}{2}} \cdot \left(\sum_{C_i=C_1}^{C_N} \sum_{\tau_i=\tau_o}^{\tau_M} S_{C_i}(\tau_i)\right)^{\frac{1}{2}}}$$

wherein $C_1 \ldots C_N$ denote N sensor measuring channels in an arbitrary topical distribution relative to said biological tissue complex $S_{C_i}(t_i)$ denotes a signal in the channel $C_i$ at a point in time $t_i$, and $\tau_o \ldots \tau_i \ldots \tau_M$ denote said time interval of a template, beginning at $\tau_o$ and ending at $\tau_M$ with samples at a time $\tau_i$ in said time interval, with $\tau_o < \tau_i < \tau_M$.

10. An arrangement as claimed in claim 1, further comprising means for connecting said means for averaging to said templates memory for supplying the output of said means for averaging to said template memory for continual updating of said template.

11. An arrangement as claimed in claim 1, further comprising means for connecting said means for averaging to said means for defining said threshold for continually updating said threshold.

12. An arrangement as claimed in claim 1, further comprising means for summing said electrical signals and for supplying the sum of said electrical signals to said means for recognizing said individual signal patterns.

13. An arrangement as claimed in claim 1, further comprising:

means for intermediately storing said correlation signal;

means for calculating a frequency histogram of the stored correlation signal;

wherein said means for forming a threshold is a means for setting a similarity threshold characteristic for the signal pattern which was the basis for the correlation signal stored in the means for intermediately storing based on a defined deviation of said frequency histogram from a Gaussian normal distribution curve; and wherein said means for comparing is a means for comparing said intermediately stored correlation signal to said similarity threshold and for enabling entry of the signal section which was the basis for the correlation signal stored in the means for intermediately storing to said means for averaging upon transgression of said similarity threshold.

14. An arrangement as claimed in claim 1, wherein said means for spatially and temporally correlating is an array processor computer means for forming said correlation signal using a fast convolution algorithm.

* * * * *